United States Patent [19]

Sitkovsky

[11] Patent Number: 5,180,662
[45] Date of Patent: Jan. 19, 1993

[54] CYTOTOXIC T LYMPHOCYTE ACTIVATION ASSAY

[75] Inventor: Michail V. Sitkovsky, Bethesda, Md.

[73] Assignee: The United States of America as represented by the Department of Health and Human Services, Washington, D.C.

[21] Appl. No.: 610,332

[22] Filed: Nov. 8, 1990

Related U.S. Application Data

[63] Continuation of Ser. No. 141,090, Jan. 5, 1990, abandoned.

[51] Int. Cl.$^5$ .................. G12Q 1/44; G01N 33/577
[52] U.S. Cl. ...................... 435/7.24; 435/19; 435/29; 435/34; 436/503; 436/548; 436/827
[58] Field of Search ............ 435/5, 7.23, 7.29, 19, 435/7.24, 19, 34, 29; 436/506, 519, 530, 548, 63, 811, 815, 503, 518, 548, 827

[56] References Cited

U.S. PATENT DOCUMENTS 4,652,532  3/1987  Bain et al. .
4,677,061  6/1987  Rose et al. .
4,783,410  11/1988  Pasternack et al. ............ 435/212 X

OTHER PUBLICATIONS

Takayama et al. J. Immunol. Meth. 104: 183–190, 1987.
Takayama et al. J. Immunol. 138: 566–569, Jan. 15, 1987.
Takayama et al. J. Immunol. 139: 1014–1021, Aug. 15, 1987.
Redelman, et al. J. Immunol. 124: 870–878, 1980.
Takayama et al, "A Novel Cytotoxic T Lymphocyte Activation Assay", J. Imm. Methods 104, 183–190 (1987).
Takayama et al, "Antigen Receptor-Triggered Secretion of a Trypsin-type Esterase from Cytotoxic T Lymphocytes...", J. Imm. 138, 566–569 (Jan. 15, 1987).
Takayama et al, "T Cell Antigen Receptor Triggered Exocytosis in Cytotoxic T Lymphocytes...", J. Imm. 139, 1014–1021 (Aug. 15, 1987).
Redelman et al, "The Mechanism of Cell-Mediated Cytotoxicity", J. Imm. 124, 870–878 (Feb. 1980).

Primary Examiner—David Saunders
Attorney, Agent, or Firm—Cushman, Darby & Cushman

[57] ABSTRACT

A method is provided for the quantitative study of cytotoxic T-lymphocyte activation by measuring secreted granule-associated BLT esterase activity after incubating the cytotoxic T-lymphocytes with activating stimuli. This method can be used to screen inhibiting (drugs) or activating agents (monoclonal antibodies) (at selected sub-optimal levels of activation of cytotoxic T-lymphocytes.

11 Claims, 6 Drawing Sheets

CYTOTOXIC T LYMPHOCYTE ACTIVATION ASSAY

This is a continuation of application No. 07/141,090, filed on Jan. 5, 1990, which was abandoned.

FIELD OF THE INVENTION

The present invention relates to a method for assaying for T lymphocyte activation and thus the study of biochemical events in cytotoxic T lymphocytes. The invention also relates to the diagnosis and monitoring of immunologic disease activity.

BACKGROUND OF THE INVENTION

Activation of cytotoxic T lymphocytes is routinely studied by following the fate of antigen-bearing target cells in, for example, the $^{51}$Cr-release assay. Although this assay is informative and easy to perform, it is not a direct assay for cytotoxic T lymphocyte activation, since the presence of another cell, a target cell, is required to provide a "read-out" system, thereby superimposing activation events in cytotoxic T lymphocytes with destructive "lethal hit" processes in the target cells.

The presence of target cells in the cell mixture greatly complicates the study of biochemical events in cytotoxic T lymphocytes. For example, the use of target cells as an activating stimulus does not allow control of the proportion of activated cytotoxic T lymphocytes, because of the relatively low efficiency of engagement of cytotoxic T lymphocytes in the cytotoxic T lymphocyte-target cell conjugates, as well as the difficulties in manipulating the density of activating ligand on the surface of the target cells.

SUMMARY OF THE INVENTION

It is an object of the present invention to overcome deficiencies in the prior art, such as those mentioned above.

It is another object of the present invention to provide an improved assay of cytotoxic T lymphocyte activation.

It is a further object of the present invention to provide a method for screening inhibiting agents for cytotoxic T lymphocytes.

It is yet a further object of the present invention to provide a method for screening activating agents for cytotoxic T lymphocytes.

Other objects of the invention include providing improved diagnosis and monitoring of immunologic disease activity; an improved method of triggering the secretion of granule-associated enzymatic activity in cytotoxic T-lymphocytes; and improved methods for screening drugs and monoclonal antibodies.

Exocytosis of granules is considered to be involved in the cytotoxic T lymphocyte effector functions, and trypsin-like serine esterase (BLT esterase) was recently described as being an easily detectable biochemical marker of these granules. Biochemical and morphological evidence have now been provided using other intragranule markers such as beta-glucuronidase, $^3$H-DFP labelled proteins, and Percoll gradient centrifugation, that support the use of BLT-E secretion as a assay for granule exocytosis in cytotoxic T lymphocytes.

It has been shown that the secretion of BLT-E is triggered by incubating cytotoxic T lymphocytes with antigen-bearing target cells, or with immobilized anti-monoclonal antibody to the antigen receptor of T lymphocytes. Therefore, secretion of BLT-E can be used as a convenient "read-out" assay in biochemical studies of cytotoxic T lymphocyte activation.

According to the present invention, cytotoxic T lymphocyte activation can be quantitatively assayed. This assay is based on the measurement of secreted granule-associated enzymes (BLT-esterase) produced after incubation of the cytotoxic T lymphocytes with activating stimuli.

Immobilized monoclonal antibody against the antigen receptor of cytotoxic T lymphocyte (anti-TcR mAb), concanavalin A or a combination of $4_{beta}$-phorbol 12-myristate 13-acetate (PMA) and ionophore A23187, were able to trigger secretion of enzyme in the absence of target cells. Soluble anti-TcR mAb alone did not activate the cytotoxic T lymphocytes, but using their conjugate with immobilized rabbit anti-mouse Ig antibody (RAMIIg), TcR-mediated secretion of BLT-esterase was detected.

The use of nonionic detergents Nonidet P-40 or Triton X-100 (0.0125-0.2%) did not affect the measurements of BLT-esterase activity.

The intensity of cytotoxic T lymphocyte response varies markedly with changes in the buffer systems, culture media, and additions of proteins. The intensity of secretion can be easily manipulated by changing the surface density of immobilized anti-TcR mAb, thereby providing the possibility for screening inhibiting or activating agents, such as drugs or monoclonal antibodies, at selected sub-optimal levels of CTL activation.

Since the secretion of BLT-E reflects exocytosis of granules from cytotoxic T-lymphocytes, the process of the present invention can be used for the detection of secretion of other markers of granules.

DETAILED DESCRIPTION OF THE INVENTION

The present invention is directed to a method for assaying for cytotoxic T lymphocyte activation, screening activation agents for T lymphocytes, etc., comprising incubating the cytotoxic T lymphocytes with activating stimuli and measuring the secreted granule-associated enzyme resulting from such stimulation. More specifically, the present invention comprises incubating cytotoxic T lymphocytes with antigen-bearing target cells or with immobilized monoclonal antibody to the antigen receptor of T lymphocytes, and measuring the amount of BLT-esterase secreted by the T lymphocytes.

Cytotoxic T-lymphocyte clones 2C, OE4, and BM10-37 were maintained in RPMI-1640 medium (or modified DMEM medium for that OE4 clone) supplemented with irradiated stimulator cells and an interleukin-2-containing culture supernatant. CTL clones were usually used on day four after stimulation with irradiated spleen cells and interleukin-2. CTL clones were isolated from dead feeder cells by Ficoll-Hypaque centrifugation shortly before being used in assays. Clone 2C is specific for H-2L$^d$, BM10-37 for H-2Kb, and OE4 for H-2Kd.

Preparation of Cytotoxic T-lymphocyte Lysate

For that preparation of the cytotoxic T-lymphocyte lysate, $2 \times 10^6$ CTL OE4 cells were washed and suspended in 0.5 ml of phosphate buffered saline. This suspension was frozen with liquid nitrogen and thawed by warming at 37° C. using a water bath. This freezing-thawing procedure was repeated twice. The homogenate was spun $10,000 \times g$ for ten minutes, and the supernatant was used at cytotoxic T-lymphocyte lysate equivalent to $4 \times 10^6$ CTL/ml.

Monoclonal Antibodies $V_{beta8}$-specific anti-TcR antibody F23.1 (mouse IgG2a) which reacts with 2C and OE4 CTL clones were purified by affinity chromatography using a protein-A column. Rabbit IgG anti-mouse IgG antibody was purified from lyophilized antiserum by two-step affinity chromatography using protein A-Sepharose (Pharmacia) and mouse IgG-Affi-Gel-10.

Preparation of Wells with Solid-phase Monoclonal Antibodies

The wells of a 96-well multi-well plate (sold under the tradename 'microtiter' by Dynatech, MC#2000) were coated with monoclonal anti-TcR antibodies by incubating 50 microliters of an antibody solution per well in phosphate buffered saline at 0° C. for thirty minutes. After incubation, each well was washed with RPMI-1640/10 mM HEPES/5% FCS. Visual observation of cytotoxic T-lymphocytes incubated with immobilized anti-TcR mAb under light microscopy confirmed their uniform distribution, because after four hours of incubation cytotoxic T-lymphocytes formed a monolayer of cells occupying the entire surface area where mAb were immobilized. In contrast, the cytotoxic T-lymphocytes formed small pellets in wells where no anti-TcR mAb were immobilized.

Two-step Immobilization of Anti-TcR mAb

Anti-TcR mAb was also immobilized via RAMIg as a second antibody. Fifty microliters of RAMIg solution in phosphate buffered saline at a concentration of 20 micrograms/ml was used for immobilization per each well by incubating it for thirty minutes at room temperature. After incubation, the solution was discarded and the wells were washed with 50 microliters of RPMI-1640/10 mM HEPES/5% FCS solution to block the protein binding surface of the plastic wells. Then the wells were incubated with 50 microliters of anti-TcR mAb solution in RPMI-1640/HERPES/FCS for thirty minutes at room temperature, and washed with RPMI-1640/HEPES/FCS. Immediately after washing, 100 microliters of cytotoxic T-lymphocyte suspension was added to each well, and BLT-esterase secretion was measured after four hours of incubation as described below.

Measurements of the Secretion

The amount of secreted BLT-esterase was measured using $1 \times 10^5$ cytotoxic T-lymphocytes in 0.1 ml of RPMI-1640 supplemented with 10 mM HEPES, 5% fetal calf serum in a 96-well multi-well plate (sold under the tradename 'microtiter' by Dynatech, MC#2000) in the presence of soluble stimuli or in wells coated with mAb F23.1. After four hours of incubation at 37° C. under 5% CO2, the cells were resuspended by gentle pipetting and were centrifuged at $200 \times g$ for 0.5 minutes. Fifty microliter aliquots of supernatant were used to assay BLT-esterase activity. The total cellular content of the enzyme was determined using 0.1% Triton X-100 solubilized cells. Determinations were carried out in triplicate.

The data are presented as a specific percentage of enzymatic activity released, which was calculated from the following equation:

% release $= 100 \times (E-S)/(T-S)$ wherein

E represents the number of enzyme units in the supernatants of the well containing stimuli;

S is the number of enzyme units in the supernatants of the well containing no stimuli;

T is the total number of units of BLT esterase in CTL per well.

The total BLT esterase content in target cells P815 and EL4 was always less than 1% of that in cytotoxic T-lymphocytes.

BLT esterase activity was measured using a minor modification of the method of Coleman and Green (1981). Briefly, 0.05 ml of culture medium was mixed with 0.95 ml of N-alpha-benzyloxycarbonyl-L-lysine thiobenzyl ester (BLT) solution (0.2 mM BLT, 0.22 mM 5,5'-dithio-bis-(2-nitrobenzoic acid) (DTNB) in phosphate buffered saline at pH 7.2. The mixture was incubated at 37° C. for twenty minutes, and the reaction was stopped by adding 5 microliters of 0.1M phenylmethanesulfonyl fluoride (PMSF) which was dissolved in dimethylsulfoxide. The solution was diluted with 1.0 ml of PBS and absorbance at 412 nm was measured in comparison a blank solution (RPMI-1640, 10 mM HEPES, 5% FCS) that was treated exactly as was the experimental solution. Since components of the culture medium do not react with DTNB the experimental absorbance value minus the blank absorbance value is proportional to the BLT esterase activity. To evaluate the contribution of dead cells to the BLT esterase measurement, cytosolic enzyme lactate dehydrogenase (LDH) activity was measured.

For quantitative measurement of granule secretion from cytotoxic T-lymphocytes, it is essential to use linear portions of the concentration dependence of the enzyme activity in a final readout system. To determine the length of the incubation period and the optimal amount of cell-equivalents needed for measuring the enzyme activity in the BLT-esterase secretion assay, the time course and dose dependence of BLT esterase activity were examined.

Figure 1A:
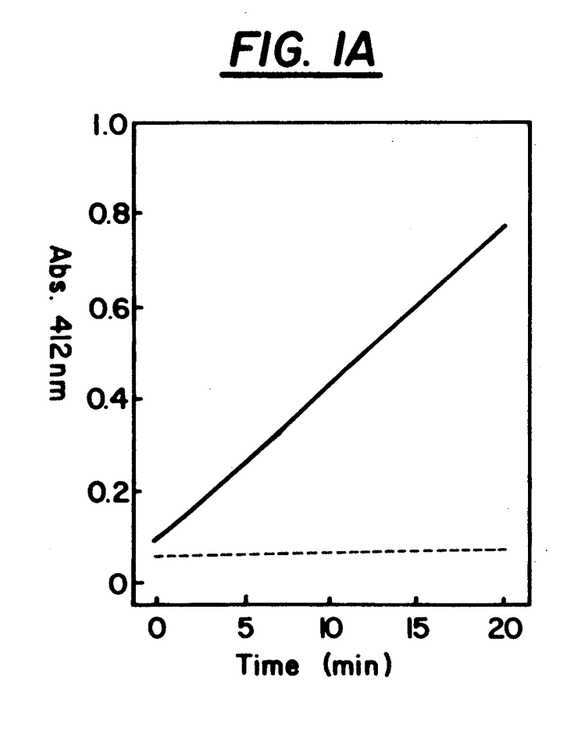
FIG. 1A shows the linearity of the time course of BLT esterase activity.
Figure 1B:
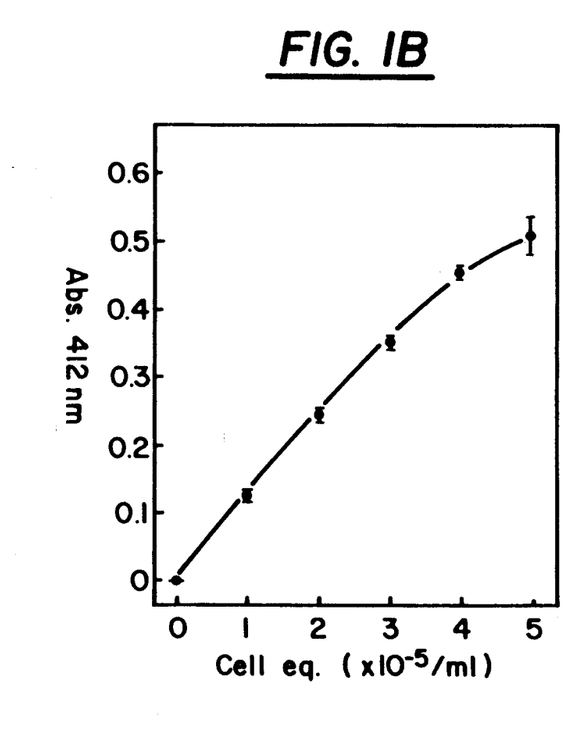
FIG. 1B shows the linearity of the dose-dependency of BLT esterase activity.

The activity of BLT esterase in cytotoxic T-lymphocyte extracts was linear in time, at least up to twenty minutes of incubation, as shown in FIG. 1A. Therefore, routinely twenty minutes of incubation was used for BLT-esterase assay, which is the final step of the secretion assay. The linear increase of absorbance was also detected up to $2.5 \times 10^5$ cell-equivalents/ml when different dilutions of cytotoxic T-lymphocytes were used for BLT esterase assay, as shown in FIG. 1B.

In FIG. 1, Panel A shows the time course of BLT esterase activity in CTL lysate. The solid line shows eighty microliters of CTL lysate which were equivalent to $5 \times 10^5$ cells/ml mixed with 1.52 ml of 0.2 mM BLT, 0.22 mM 5,5'-dithio-bis-(2-nitrobenzoic acid) (DTNB) containing (phosphate buffered saline) ΓBS (BLT/DTNB/PBS). The reaction was monitored by Beckman DU-50 spectrophotometer. The dotted line shows the spontaneous BLT cleavage which was measured when 80 microliters of blank solution were treated exactly the same as the CTL lysate.

In panel B, fifty microliters of CTL lysates, which were equivalent to the cell concentration indicated on the abscissa, were mixed with 0.95 ml of BLT/DTNB/PBS, and incubated at 37° C. for fifteen minutes. The reaction was terminated by the addition of 5 microliters of 0.1M phenylmethanesulfonyl fluoride (PMSF), and the mixture was diluted with 1.0 ml of PBS. The absorbance at 412 nm is shown.

The limiting factor in the sensitivity of the assay is the amount of secreted enzymatic activity. Since the results of the BLT esterase secretion assay are presented as a percentage of secreted enzyme activity over the total amount of enzyme activity per cell, which was determined after solubilization of the cells, it was necessary to estimate the effect of cell solubilization on the enzymatic activity of BLT esterase.

Figure 2:
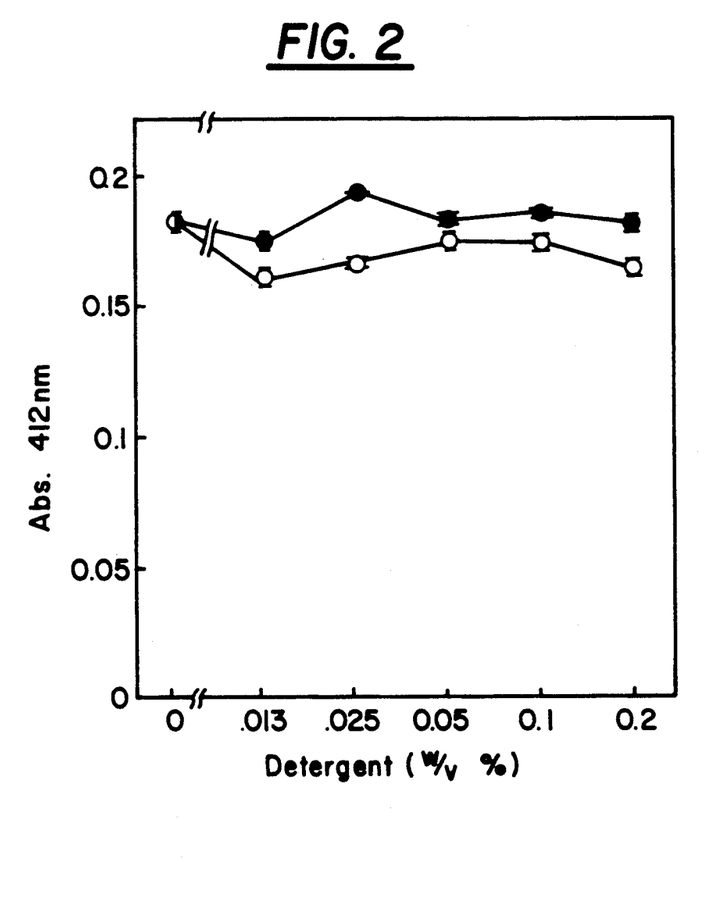
FIG. 2 shows the effect of nonionic detergents on BLT-esterase activity in cytotoxic T-lymphocyte extracts.

Cytotoxic T-lymphocytes solubilized with non-ionic detergents such as Triton X-100 or Nonidet P-40 were routinely used in the present study to measure the total amount of BLT esterase per cell. Therefore, the effect of these detergents on the measurements of BLT esterase activity was examined, cf. FIG. 2. To obtain the results shown in FIG. 2, CTL lysate was prepared by extracting $2 \times 10^5$ cells/ml with different concentrations of Triton X-100 (■——■) or Nonidet P-40 (O——O). After fifteen minutes of incubation, 50 microliters of sample were mixed with 0.95 ml of BLT/DTNB/PBS and incubated for fifteen minutes at 37° C. The reaction was terminated and the absorbance was measured as described in FIG. 1, panel B. The activity of BLT-E at "zero" concentration of detergents represents the activity of BLT-E in CTL lysates obtained by freezing-thawing of CTL. As can be seen from FIG. 2, the presence of Nonidet P-40 and Triton X-100 in cell extracts did not have any effect on the enzymatic activity up to 0.2%, since the same total BLT esterase activity was measured in cells disrupted by freezing-thawing or by extraction with nonionic detergents. Because of this phenomenon, 0.1% Triton X-100 or 0.1% Nonidet P-40 were routinely used for cell solubilization, and total content of BLT esterase in cytotoxic T-lymphocytes was measured using 0.1% non-ionic detergent-solubilized material which was diluted to $2.5 \times 10^5$ cell equivalent/ml.

Figure 3:
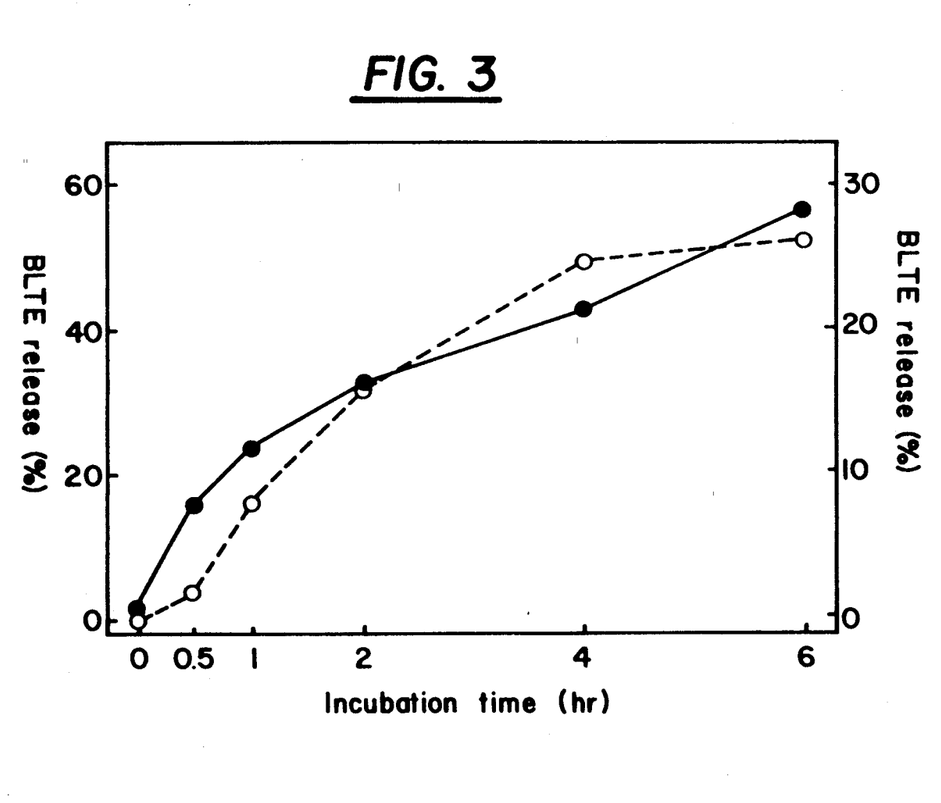
FIG. 3 shows the time-course of BLT esterase secretion by cytotoxic T-lymphocyte clone 2C stimulated with solid-phase anti-TcR mAb (O———O) or by CTL clone BM10-37 stimulated with PMA/A23187 (●———●).
Figure 4A:
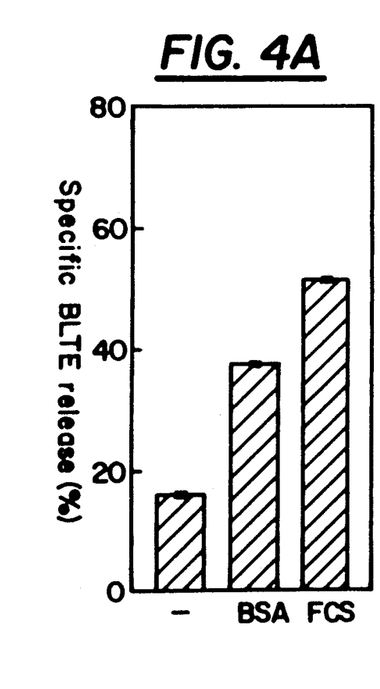
FIGS. 4A-4D shows the effect of incubation of CTL in media of different composition on BLT esterase secretion.
Figure 4B:
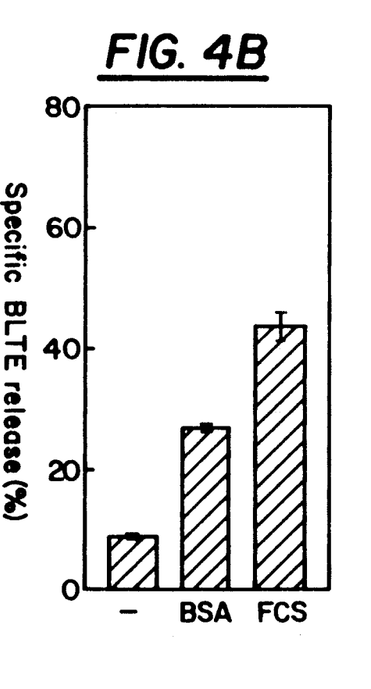
Figure 4C:
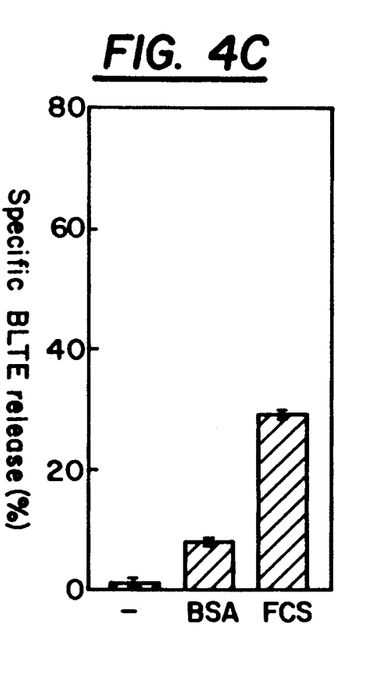
Figure 4D:
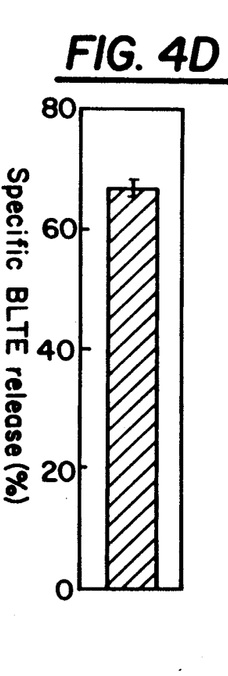

Studies of the time-course of BLT esterase secretion by cytotoxic T-lymphocyte clones, triggered by the synergistic action of PMA and ionophore A23187 or anti-TcR mAb are presented in FIG. 3. In FIG. 3, $1 \times 10^5$ CTL were incubated in 0.1 ml of RPMI-1640/10 mM HEPES/5% fetal calf serum (FCS) in the presence of 4beta-phorbol 12-myristate 13-acetate (PMA) (10 ng/ml)/A23187 (0.5 microgram/ml) or immobilized F23.1. After the incubation periods indicated on the abscissa, BLT esterase activity in the supernatant was measured as described below. Treatment of cytotoxic T-lymphocytes with OMA and A23187 results in faster release of granule enzyme than during incubation with immobilized anti-TcR mAb=F23.1. A similar time course of BLT esterase release was found for different cytotoxic T-lymphocyte clones, and any time point between two and four hours of incubation can be used for termination of the assay in studies of the effect of inhibiting and activating stimuli on cytotoxic T-lymphocyte activation. Even shorter incubations can be used when the only goal of the assay is detection of cytotoxic T-lymphocyte activation (e.g., in studies of antigen-specificity of cytotoxic T-lymphocytes).

Since TcR-triggered exocytosis requires an extracellular $Ca^{++}$, and exocytosis activating pathway is counteracted by cAMP-mediated inhibitory pathways, it would be expected that the composition of the incubation medium may influence the intensity of the TcR-triggered secretion. Therefore, the effect of several of the most often used incubation and culture media on cytotoxic T-lymphocyte exocytosis was studied, as shown in FIG. 4.

In FIG. 4, the CTL clone OE4 was stimulated with solid-phase F23.1 mAb for four hours in different media in the absence of supplement protein ($-$), in the presence of 01. mg/ml BSA, or 5% fetal calf serum (FCS). 0.1 microgram of F23.1 mAb were used for immobilization per well. The following culture media were used in the present experiment:

panel A, RPMI-1640 with 10 mM HEPES, pH 7.2;
panel B, Hank's balanced salt solution with 10 mM HEPES, pH 7.2;
panel C, Krebs-Ringer's phosphate buffer solution;
panel D, K2-medium consisting of Eagle's Hank's amino acid solution (EHAA, Biofluids), non-essential amino acid supplement and 10% FCS.

Figure 5:
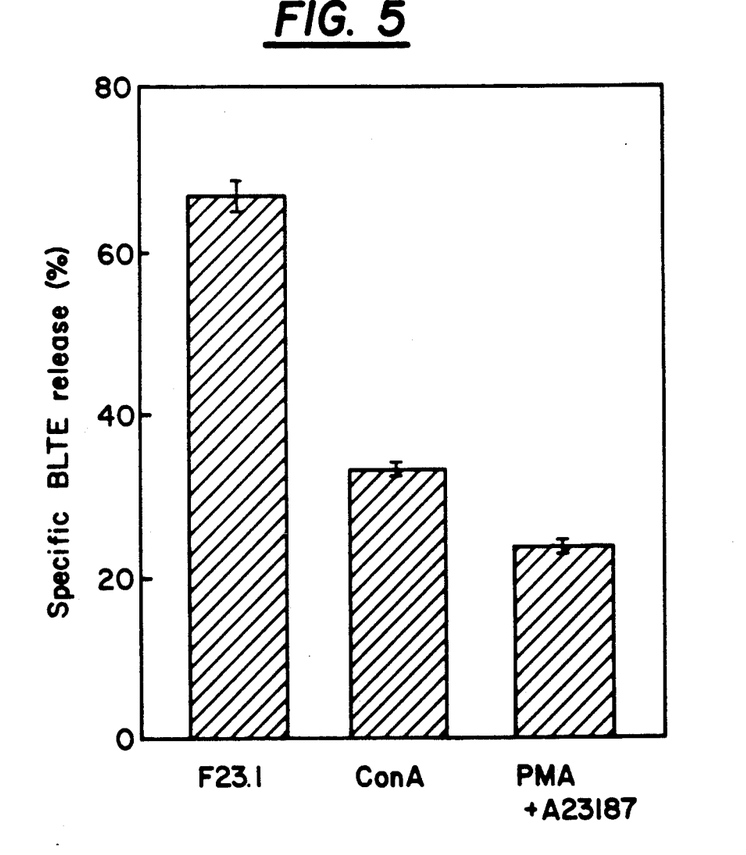
FIG. 5 shows triggering of BLT-esterase secretion in CTL clones by concanavalin A, immobilized anti-TcR mAb and PMA/A23187.

To demonstrate triggering of BLT-esterase secretion in CTL clones by concanavalin A, immobilized anti-TcR mAb and PMA/A23187, $1 \times 10^5$ per well of CTL clone OE4 were incubated in RPMI-1640/10 mM HEPES/5% FCS for four hours in wells of 96 well microtiter plates with 0.1 microgram per well during immobilization of solid-phase F23.1 with anti-TcR mAb or with 0.2 microgram per well during immobilization of solid-phase concanavalin A, or with 10 ng/ml of PMA/0.5 micrograms/ml A23187. The activity of secreted BLT esterase in the supernatants was measured as described below. A negligible release of BLT esterase was detected in this experiment when cytotoxic T-lymphocytes were incubated without stimuli.

FIG. 4 shows that while TcR-triggered secretion could be detected in all tested incubation media, the addition of exogenous protein greatly increased the detectable level of secreted BLT esterase, and fetal calf serum had a greater enhancing effect than BSA. The maximum secretion was detected when cytotoxic T-lymphocytes were incubated in RPMI-1640 media, supplemented with 2-mercaptoethanol, 10% FCS, 10 mM HEPES, and non-essential amino acids (K-2 medium in a 1:1 mix with EHAA culture medium).

Different stimulating agents, such as lectins, mAb to different surface antigens, target cells, pharmacological agents, were extensively tested for their ability to trigger secretion of granule-associated enzymes. Among these agents, only concanavalin A (Con A), immobilized mAb to TcR (both clonotypic and against $T_{beta8}$-region of TcR) and protein kinase C activators in synergy with $Ca^{++}$ ionophores were able to induce secretion, as shown in FIG. 5. The lower efficiency of Con A in secretion triggering in comparison with anti-TcR mAb could be explained by interactions of Con A not only with TcR, but also with other proteins on the surface of the cytotoxic T-lymphocytes, including LFA-1, T200, and possible T3 antigens. It was shown that TcR-crosslinking triggers release of intragranular markers such as BLT esterase, beta-glucuronidase, and 29KDa 3H-DFP labelled polypeptide, while no changes in release of cytoplasmic marker, lactate dehydrogenase (LDH), was detected.

As shown in Table 1, the plasticware is important for the triggering of secretion by immobilized mAb, most likely due to a different ability of mAb to be immobilized on the surface of the different plastic vials or due to different adherence of cytotoxic T-lymphocytes. For analytic screening purposes, the optimal conditions of exocytosis triggering were observed when wells of 96 U-bottom well multi-well plates (sold under the tradename 'microtiter' by Dynatech. MC-200) were precoated with 50 microliters of mAb solution (2 micrograms/ml in phosphate buffered saline) followed by the addition of $1 \times 10^5$ cells in 100 microliters of K2-medium or RPMI-1640 supplemented with 5% fetal calf serum, 10 mM HEPES. When a large number of activated cytotoxic T-lymphocytes is needed for consequent biochemical studies, they could be incubated with anti-TcR mAb which were immobilized in the vials or on the surface of Petri dishes.

TABLE 1

BLT-E secretion in CTL clone 2C stimulated with F23.2 which was immobilized in various plasticware

| Dishes Company | Well | Shape of Bottom | Diameter of well (mm) | Index of surface area of the wells[a] | BLT-E secretion (%) |
|---|---|---|---|---|---|
| Dynatech MC-2000 | 96 | round | 6 | (1)[b] | 38.6 |
| Dynatech Immunlon | 96 | round | 6 | (1)[b] | 26.6 |
| Costar #3596 | 96 | flat | 6 | 1 | 14.5 |
| Nunc Nunclon | 24 | flat | 15 | 6.3 | 10.0 |
| Falcon #3046 | 6 | flat | 35 | 34 | 12.3 |
| Corning #25010 | 1 | flat | 60 | 100 | 16.4 |

[a]Index of surface area represents the ratio between surface area of the bottom of the wells in a 96-well plate and other wells used. According to this index, the volume of F 23.1 solution (2 g/ml in PBS) for immobilization and the volume of CTL suspension ($1 \times 10^6$ cells/ml) for incubation were determined: volume of F23.1 solution = 50 μl × ratio, volume of CTL suspension = 100 μl × ratio.
[b]Bottom area of round-bottom wells were regarded as the same as the flat-bottom wells.
[c]CTLs ($1 \times 10^6$ cells/ml) were distributed in the wells which were precoated with F23.1. No precoated wells were used as control. The volume of the F23.1 solution for coating and the volume of CTL suspension were determined as described above. After 4 hours incubation, the medium was recovered and spun to remove cells. Fifty 1 μl aliquots of supernatant ($5 \times 10^4$ cell equivalent) were used for the BLT esterase assay and specific BLT esterase release (%) was calculated as described in the Methods.

a Index of surface area represents the ratio between surface area of the bottom of the wells in a 96-well plate and other wells used. According to this index, the volume of F23.1 solution (2 g/ml in PBS) for immobilization and the volume of CTL suspension ($1 \times 10^6$ cells/ml) for incubation were determined: volume of F23.1 solution = 50 μl × ratio, volume of CTL suspension = 100 μl × ratio. b Bottom area of round-bottom wells were regarded as the same as the flat-bottom wells. c CTLs ($1 \times 10^6$ cells/ml) were distributed in the wells which were precoated with F23.1. No precoated wells were used as control. The volume of the F23.1 solution for coating and the volume of CTL suspension were determined as described above. After 4 hours incubation, the medium was recovered and spun to remove cells. Fifty 1 μl aliquots of supernatant ($5 \times 10^4$ cell equivalent) were used for the BLT esterase assay and specific BLT esterase release (%) was calculated as described in the Methods.

When the secretion of BLT esterase was measured after incubation with solid phase anti-TcR mAb, it was found that immobilized clonotypic or anti-v-$beta 8$-region-specific anti-TcR mAb mimic antigen-bearing target cells and stimulate exocytosis of granules. The intensity of secretion is increased with the increase in density of immobilized anti-TcR mAb.

Figure 6:
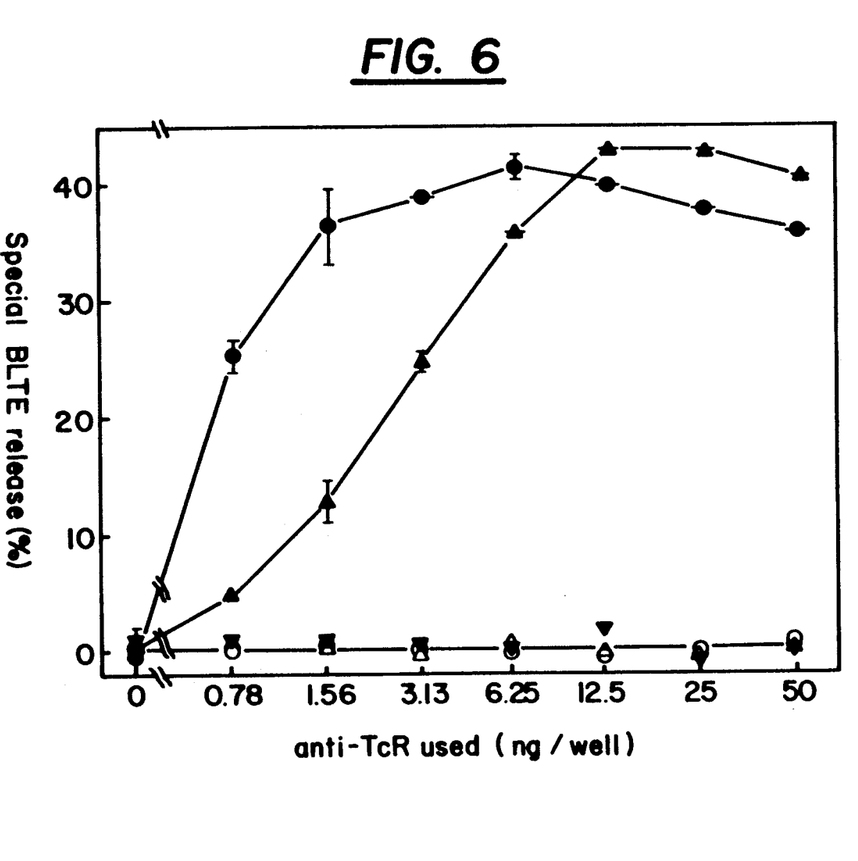
FIG. 6 shows the higher efficiency of BLT-E secretion triggering by F23.1 mAb immobilized in the wells precoated with TAMIg.

In FIG. 6, anti-TcR mAb, F23.1 (closed symbols) or irrelevant mAb, 1.B2 (open symbols) were immobilized via solid-phase rabbit anti-mouse immunoglobulin (RAMIg) (●——●, (O——O) or directly to the well (▲——▲, △——△) as described below. BLT-esterase secretion from cytotoxic T-lymphocyte close OE4 was measured after four hours of incubation at 37° C. in such wells. For a control, the wells were incubated with RPMI-1640/10 mM HEPES/5% FCS instead of RAMIg, and then incubated with F23.1 (▼-▼).

The characteristic dose-response curve for anti-TcR mAb triggered exocytosis is shown in FIG. 6. The dose-response curve in all tested cytotoxic T-lymphocyte clones demonstrates a region where a sharp increase in secretion was caused by relatively moderate changes in surface density of immobilized mAb, and such region of the dose-response curve is most suitable for the studies of the effect of different agents on cytotoxic T-lymphocyte activation. The dose-response curves of anti-TcR mAb triggered secretion are different for different cytotoxic T-lymphocyte clones. While secretion of cytotoxic T-lymphocytes is highly reproducible when compared at the same day experiment, it varies with cytotoxic T-lymphocytes harvested at different days after feeding.

Repeated attempts to induce secretion with soluble anti-TcR mAb have failed. No secretion was detected when cytotoxic T-lymphocyte clone was incubated with different concentrations of soluble F23.1 anti-TcR mAb followed by incubation with different concentrations of crosslinking soluble rabbit anti-mouse Ig antibody (RAMIg). Preformed soluble complexes between RAMIg and F23.1 at several RAMIg/antiTcR mAb ratios also were not effective in triggering BLT esterase secretion. These results suggest that crosslinking of TcR achieved by soluble F23.1 mAb even with second crosslinking antibodies (RAMIg) is not sufficient for triggering cytotoxic T-lymphocytes. It is possible that additional events, such as adhesion of cytotoxic T-lymphocytes to the plastic and subsequent cytoskeletal changes, are required for exocytosis triggering in cytotoxic T-lymphocytes.

Much lower concentrations of F23.1 anti-TcR mAb during immobilization on the well surface were required when wells were first precoated with RAMIg at concentrations of 1 microgram per well, and then incubated with different concentrations of F23.1, as shown in FIG. 6. Irrelevant, control, 1B.2 mAb (which do not react with OE4 cytotoxic T-lymphocyte clone) did not induce BLT esterase release. F23.1 mAb triggered only 15% of BLT esterase release when immobilized alone, using 1.56 Ng/Ml of diluted solution for immobilization, while about 35% BLT esterase release was observed if F23.1 solution of the same concentration was used for immobilization via immobilized RAMIg. These results suggest that either the efficiency of immobilization of F23.1 or the orientation when immobilized are greatly improved for the subsequent interactions with TcR on the cytotoxic T-lymphocyte surface.

With the assay system of the present invention, it is possible to study a variety of inhibiting or activating agents in conditions most favorable for the detection of their enhancing or inhibitory effect on TcR-regulated cytotoxic T-lymphocyte activation. One of the advantageous applications of the described system is the modelling of the cell-cell interactions by co-immobilization of protein ligands to cytotoxic T-lymphocyte cell surface proteins. Co-immobilization procedures were used to demonstrate the differences between soluble and solid-phase anti-Lyt-2-mAb in their effect on TcR-triggered exocytosis in cytotoxic T-lymphocytes.

One of the advantages of the process of the present invention is the possibility of stimulating the release of easily detectable enzymatic activity of cytotoxic T-lymphocytes by solid-phase mAb to TcR and to manipulate the intensity of cytotoxic T-lymphocyte response depending on the purpose of the activation studies. This is readily achieved by changing the surface density of immobilized anti-TcR mAb. Inhibiting and activating agents (mAb, pharmacological reagents, etc.,) can be screened with greater sensitivity when low surface density of stimulating immobilized mAb is used, and sub-optimal intensity of secretion is achieved. Using this property of anti-TcR mAb triggered exocytosis in cytotoxic T-lymphocytes, it has been shown that inhibition by anti-Lyt-2 mAb is most easily demonstrated at low surface density of stimulating anti-TcR mAb.

FIG. 3 illustrates the difference in the time-course of BLT-esterase secretion between anti-TcR mAb-triggered and PMA/A21387 treatment, especially after 30 minutes incubation of cytotoxic T-lymphocytes. This result may suggest the additional requirements in cytoskeletal and biochemical events involved in TcR-mediated cytotoxic T-lymphocyte activation as compared with the effect of PMA and A23187.

The enhancing effect of bovine serum albumin or fetal calf serum in the incubation media on the level of BLT-esterase secretion by anti-TcR mAb activated CTL, as shown in FIG. 4, suggests that secreted enzyme can be protected from inactivation by its presence, or the responsiveness of cytotoxic T-lymphocyte could be enhanced in the presence of supplemental protein.

The secretion of BLT-esterase from cytotoxic T-lymphocytes can be used as an alternative screening assay in searches mAb to surface antigens of cytotoxic T-lymphocytes. MAb can be tested for in hybridoma supernatants for inhibition of anti-TcR mAb triggered BLT-esterase secretion or for activation of exocytosis of granules from cytotoxic T-lymphocytes in the presence of Fc-receptor bearing target cells. This provides a method for isolating yet undiscovered and previously missed mAb against antigen receptors of T-lymphocytes neighboring molecules.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology employed herein is for the purpose of description and not of limitation.

What is claimed is:

1. A method for directly assaying cytotoxic T lymphocyte activation comprising the steps of:
   1) incubating cytotoxic T lymphocytes with one or more lymphocyte activating stimuli selected from the group consisting of immobilized anti-TcR monoclonal antibody, an immunocomplex of anti-TcR monoclonal antibody and immobilized rabbit anti-mouse antibody, a mixture of beta-phorbol-12-myristate-13 acetate and ionophore A23187, and immobilized concanavalin A, said activating stimuli inducing the exocytosis of cytotoxic T lymphocyte granules and resulting in the secretion of BLT-esterase; and
   2) quantitatively or qualitatively measuring the secretion of said BLT-esterase resulting from the activation of cytotoxic T lymphocyte by the lymphocyte activating stimuli.

2. The method of claim 1 wherein a supplemental, lymphocyte activation-enhancing protein containing composition is added at step 1), said protein containing composition being selected from the group consisting of bovine serum albumin (BSA) and fetal calf serum (FCS).

3. The method of claim 1, wherein said immobilized anti-TcR monoclonal antibody consists of a support-immobilized first monoclonal antibody (mAb), said first mAb being immobilized directly or indirectly via a second or additional mAb to said support.

4. The method of claim 3, wherein said immobilization occurs on a solid support comprising a multi-well plate.

5. The method of claim 3, wherein the surface of said support whereon said mAb is immobilized consists essentially of plastic.

6. The method of claim 1, wherein the secretion of said BLT-esterase is measured as a function of enzymatic activity.

7. The method of claim 6, wherein said enzymatic activity is caused by a reaction of N-alpha-benzyloxycarbonyl-L-lysine thiobenzyl ester with (BLT) esterase activity.

8. The method of claim 7, wherein said enzymatic activity is measured by:
   1) mixing said secreted BLT esterase with BLT and 5,5a'-dithio-bis-(2-nitrobenzoic acid) (DTNB);
   2) incubating the mixture of step 1); and
   3) measuring the absorbance of said incubated mixture at 412 nm by spectrophotometric analysis.

9. The method of claim 8, wherein phenylmethanesulfonyl fluoride (PMSF) is added to the mixture of step 2) prior to spectrophotometric analysis.

10. A method for screening monoclonal antibodes or pharmacological agents for cytotoxic T lymphocyte activation comprising the steps of:

1) incubating cytotoxic T lymphocytes with one or more monoclonal antibodies or pharmacological agents;

2) quantitatively or qualitatively measuring the exocytosis of cytotoxic T lymphocyte granules by the resulting secretion of BLT-esterase, said secretion, if any, being induced by cytotoxic T lymphocyte activating monoclonal antibodies or pharmacological agents.

11. A method for screening monoclonal antibodies or pharmacological agents for use in inhibiting activation of cytotoxic T lymphocytes comprising the steps of:

1) incubating cytotoxic T lymphocytes with:

a) one or more monoclonal antibodies or pharmacological agents, and b) one or more lymphocyte activating stimuli selected from the group consisting of immobilized anti-TcR monoclonal antibody, an immunocomplex of anti-TcR monoclonal antibody and immobilized rabbit anti-mouse antibody, a mixture of beta-phorbol-12-myristate-13 acetate and ionophore A23187, and immobilized concanavalin A, said activating stimuli inducing the exocytosis of cytotoxic T lymphocyte granules resulting in the secretion of BLT-esterase; and 2) quantitatively or qualitatively measuring the exocytosis of cytotoxic T lymphocyte granules by the resulting secretion, if any, of BLT-esterase.

* * * * *

UNITED STATES PATENT AND TRADEMARK OFFICE
CERTIFICATE OF CORRECTION

PATENT NO. : 5,180,662
DATED : JANUARY 19, 1993
INVENTOR(S) : MICHAIL V. SITKOVSKY

It is certified that error appears in the above-indentified patent and that said Letters Patent is hereby corrected as shown below:

On the title page, item [63] and column 1, line 6, please correct the filing date by replacing "1990" with --1988--.

Signed and Sealed this

Fourth Day of January, 1994

Attest:

BRUCE LEHMAN

*Attesting Officer*  *Commissioner of Patents and Trademarks*